Oct. 20, 1942. L. B. CODDINGTON Plant Pat. 552
ROSE PLANT
Filed April 23, 1942
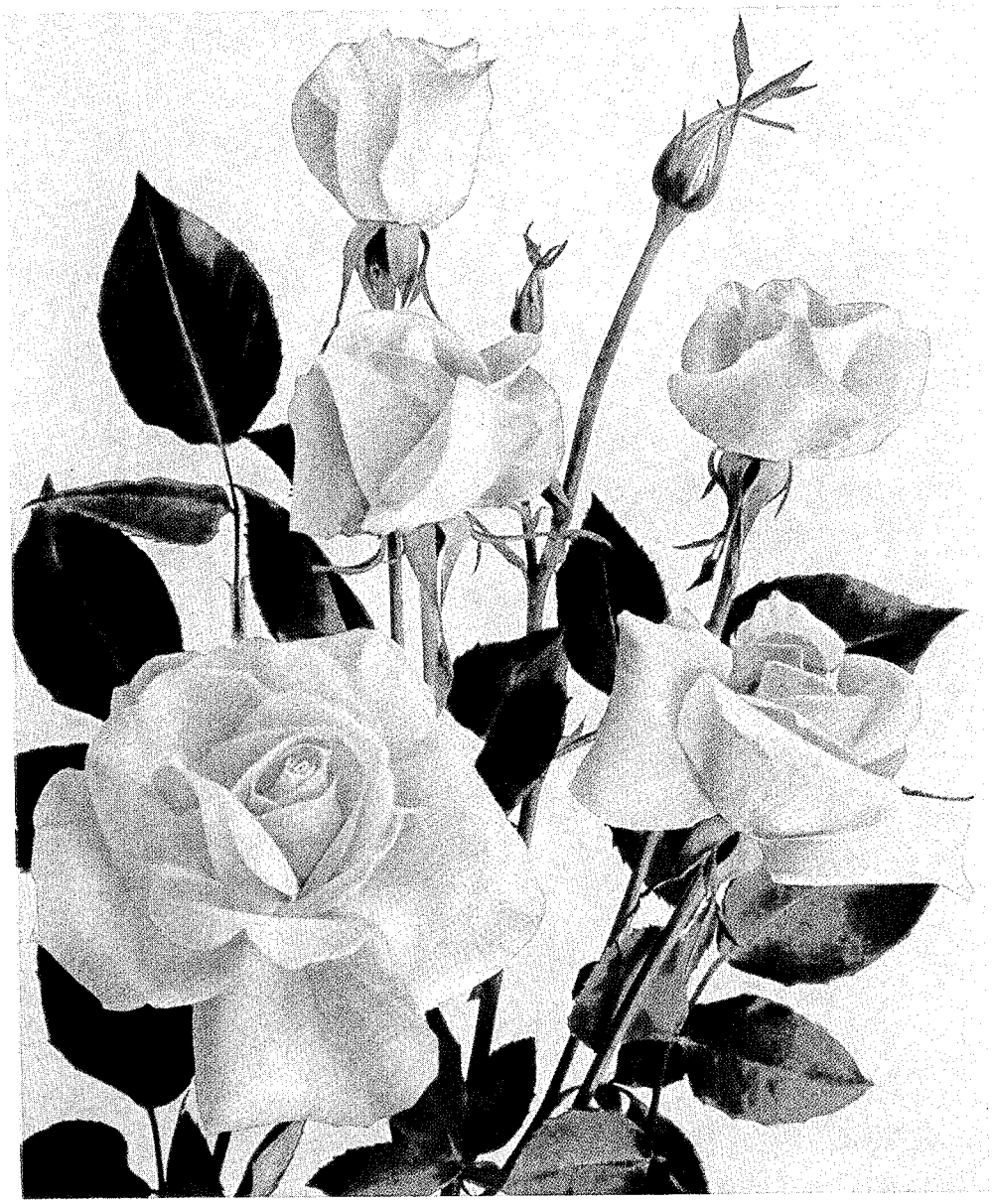
Inventor
L. B. Coddington
By Robb & Robb
Attorneys Patented Oct. 20, 1942

Plant Pat. 552

UNITED STATES PATENT OFFICE

552

ROSE PLANT

Lyman B. Coddington, Murray Hill, N. J., assignor to L. B. Coddington Co., Murray Hill, N. J., a corporation of New Jersey Application April 23, 1942, Serial No. 440,245

1 Claim. (Cl. 47—61)

The present discovery relates to a new and distinct variety of hybrid tea rose plant, originating as a sport of the variety "Royal Beauty," the subject-matter of my prior Patent No. 452, dated February 25, 1941.

The primary distinction of the new sport, discovered by me growing upon the parent in my possession, is found in the mutation as to color of the blossoms. The blossom of the parent plant, as the calyx breaks, is red, whereas this sport at the same stage is Rose Doree (Plate I, Ridgway's) blending toward the base with Strawberry Pink (same plate), while at the stage of the freshly opened flower the color changes to tones of Tyrian Rose and Rose Color with Rose Red (Plate XII) in the depths, finally becoming lighter, as the flower matures, with outside petals reaching tones of Spinel Pink (Plate XXVI) and Deep Rose Pink (Plate XII), as distinguished from the red color tones of its parent. In general tonality, the present rose is characterized as to novelty by its live or beautiful pink color, as distinguished from the red color of its parent.

The sport retains the strong, spicy fragrance of the parent, but is otherwise different in the development of larger blossoms on an overall average and a decidedly greater number of petals, thereby producing a very attractive appearance for a variety in the pink range of color, especially for cut flower purposes.

Other less important distinctions from its parent and similar varieties may be noted in the following detailed description, in which color terminology used conforms to Ridgway's Color Standard where plate numbers are given; otherwise to general dictionary terminology.

Type: Half hardy; tall bush; greenhouse; outdoor; sport; for cut flowers.
Class: Hybrid tea.
Breeding or discovery: Sport.
*Parent.*—"Royal Beauty."
*Propagation.*—Holds its distinguishing characteristics through succeeding propagations by cuttings, grafting, and budding.

*Flower*

Locality where grown: Murray Hill, New Jersey.
Flowers borne: Singly, on strong, long stems.
Quantity of bloom: Free in greenhouse; averages 22 blooms per season.
Continuity: Continuous.
Fragrance: Strong; spicy.

Bud:
*Peduncle.*—Medium length; medium heavy; erect; stiff; Green; almost smooth; few green prickles.
*Before calyx breaks.*—*Size*—medium. Form—long; pointed; with slender foliaceous parts extending beyond the tip of the bud equal to three-fourths of its length of one and one-half inches.
*As calyx breaks.*—Rose Doree, Plate I, blending toward base with Strawberry Pink, Plate I.
*As first petal opens.*—Size—medium. Form—pointed. Opening—opens up well. Under ordinary conditions, has very good lasting qualities.

Bloom:
*Size, when fully open.*—Large; six and one-half inches (overall average, four inches).
*Petalage.*—Semi-double; from 36 to 38 petals (perfect); arranged regularly.
*Form.*—Cupped; high center at first; becoming open, cupped, high centered; petals remaining at first and later at maturity, loosely cupped inward.

Petals: Thick; satiny.
*Shape.*—Outside, intermediate and inside—ovate.

This description of a newly opened flower was made from a rose grown in a greenhouse, in December, 1941, at Murray Hill, New Jersey:
*Color.*—Tones of Tyrian Rose and Rose color, Plate XII, with Rose Red, Plate XII, in the depths. Mature flower becomes lighter, with outside petals reaching tones of Spinel Pink, Plate XXVI, and Deep Rose Pink, Plate XII.
*Flower longevity.*—As cut roses grown in greenhouse in December—four to five days. Kept in ice-box twelve days with color still fine.

*Reproductive organs*

Stamens: Many, arranged regularly about pistils.
Filaments: Medium length; White.
Anthers: Medium size; Yellow.
Pollen: Abundant; Gold.
Pistils: Many.
Styles: Uneven; medium length; medium heavy; separated.
Stigma: White.
Ovaries: Enclosed in calyx.
Hips: Short; globular, with inconspicuous neck; Green; smooth; thin walls.

Sepals: Permanent; moderately long; spear-shaped.
Seeds: Large, six to eight to pod.

*Plant*

Foliage:
*Leaves.*—Compound of five leaflets; large; leathery; Yew Green, Plate XXXI; petioles and part of mid-rib touched with Brick Red, Plate XIII.
*Leaflets.*—Ovoid; margin simply serrate.
*Rachis.*—Heavy. Upper side — grooved; prickly. Under side—prickly.
*Stipules.*—Long; medium width; with long points turning out at an angle of 45°.
*Disease.*—Resistant to mildew and blackspot.

Growth:
*Habit.*—Upright; branched.
*Growth.*—Free; vigorous.
*Canes.*—Medium heavy.
*Stems.*—Tones of Courge Green, Plate XVII, and Lettuce Green, Plate V, with some Pompeian Red, Plate XIII, on the stems which disappears as the flowers mature. *Thorns.*—Few; medium length; hooked downward, with narrow base. *Prickles.*—none. *Hairs.*—None.
*Branches.*—*Thorns*—few; medium length; hooked downward, with narrow base.
*New shoots.*—*Thorns*—few; medium length; hooked downward, with narrow base. *Prickles*—none. *Hairs*—none.

I claim:

A new and distinct variety of rose plant, characterized as to novelty by the brilliant pink color of the blossoms, their large size and great number, combined with the strong, spicy fragrance of the flowers and free blooming habit of the plant, substantially as shown and described.

LYMAN B. CODDINGTON.